US008474635B2

(12) United States Patent
Johnson

(10) Patent No.: US 8,474,635 B2
(45) Date of Patent: Jul. 2, 2013

(54) ENDODONTIC PROCEDURE EMPLOYING SIMULTANEOUS LIQUEFACTION AND ACOUSTIC DEBRIDEMENT

(76) Inventor: Douglas B. Johnson, Tulsa, OK (US)

( * ) Notice: Subject to any disclaimer, the term of this patent is extended or adjusted under 35 U.S.C. 154(b) by 60 days.

(21) Appl. No.: 13/279,979

(22) Filed: Oct. 24, 2011

(65) Prior Publication Data

US 2012/0040306 A1 Feb. 16, 2012

Related U.S. Application Data

(63) Continuation of application No. 12/255,280, filed on Oct. 21, 2008, now Pat. No. 8,043,088, which is a continuation-in-part of application No. 11/130,081, filed on May 16, 2005, now abandoned.

(51) Int. Cl.
*A61C 5/02* (2006.01)

(52) U.S. Cl.
USPC ......................................... 215/224

(58) Field of Classification Search
USPC .............. 433/81, 86, 102, 119, 166, 215, 224
See application file for complete search history.

(56) References Cited

U.S. PATENT DOCUMENTS

| 4,012,842 | A | 3/1977 | Vit |
| 4,019,254 | A | 4/1977 | Malmin |
| 4,229,168 | A | 10/1980 | Scholz, Jr. |
| 4,247,288 | A | 1/1981 | Yoshii |
| 4,330,278 | A | 5/1982 | Martin |
| 4,370,131 | A | 1/1983 | Banko |
| 4,492,574 | A | 1/1985 | Warrin |
| 4,505,676 | A | 3/1985 | Gonser |
| 4,571,183 | A | 2/1986 | Nash |
| 4,617,918 | A | 10/1986 | Donohue |
| 4,681,545 | A | 7/1987 | Lapcevic |
| 4,818,229 | A | 4/1989 | Vasile |
| 5,116,227 | A | 5/1992 | Levy |
| 5,320,530 | A | 6/1994 | Fong |
| 5,531,597 | A | 7/1996 | Foulkes |
| 5,567,153 | A | 10/1996 | Foulkes |
| 5,775,901 | A | 7/1998 | Riso |
| 5,853,290 | A | 12/1998 | Winston |
| 5,868,570 | A | 2/1999 | Hickok |
| 6,050,818 | A | 4/2000 | Boland |
| 6,162,202 | A | 12/2000 | Sicurelli |
| 6,948,935 | B2 | 9/2005 | Nusstein |
| 2003/0157458 | A1 | 8/2003 | Buchanan |
| 2003/0207231 | A1 | 11/2003 | Nance |
| 2004/0038175 | A1 | 2/2004 | Hickok |
| 2004/0126732 | A1 | 7/2004 | Nusstein |
| 2006/0257819 | A1 | 11/2006 | Johnson |
| 2008/0044789 | A1 | 2/2008 | Johnson |

OTHER PUBLICATIONS

Extended European Search Report issued by the European Patent Office, Munich, Germany, dated Feb. 17, 2010 (6 pages).

*Primary Examiner* — Cris L Rodriguez
*Assistant Examiner* — Hao D Mai
(74) *Attorney, Agent, or Firm* — Gable Gotwals

(57) ABSTRACT

An ultrasonic liquefaction endodontic system having a graspable hand piece includes a contra-angle tip assembly that has an insert and an internal fluid flow passageway. A portion of the fluid flow passageway passes through a C-shaped receiver located at the end of the receiver so that an ultrasonic frequency may pass directly to the fluid flowing through the passageway. The fluid flow passageway may be an injection tube and the tubular body portion of the tip assembly may be injection molded around the injection tube and the insert. A supply tube, which is held in position by tube guides connected to the hand piece, provides a source of flushing fluid with and without pulsed pressure. The fluid pressure pulses may have an ultrasonic energy superimposed thereon as the fluid is forced into a root canal.

7 Claims, 4 Drawing Sheets

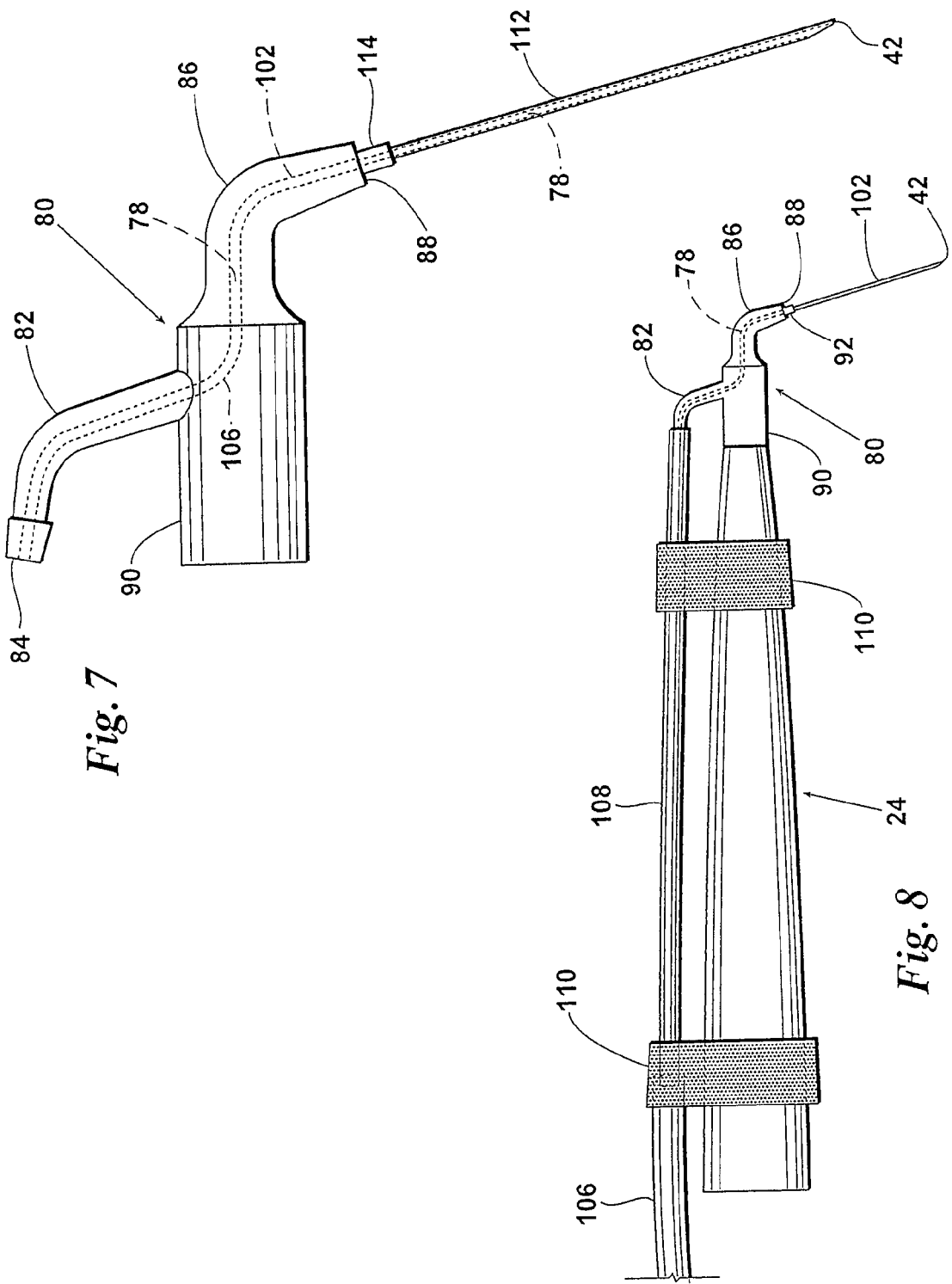

US 8,474,635 B2

ENDODONTIC PROCEDURE EMPLOYING SIMULTANEOUS LIQUEFACTION AND ACOUSTIC DEBRIDEMENT

REFERENCE TO PENDING APPLICATIONS

This application is a continuation application claiming priority to U.S. Patent application Ser. No. 12/255,280, filed Oct. 21, 2008, which was a continuation-in-part application that was based on U.S. patent application Ser. No. 11/130,081, filed May 16, 2005.

REFERENCE TO MICROFICHE APPENDIX

This application is not referenced in any microfiche appendix.

FIELD OF THE INVENTION

This invention relates to endodontic root canal preparation achieved by simultaneous liquefaction and acoustic debridgement.

BACKGROUND OF THE INVENTION

This invention relates to dental instruments and particularly to endodontic instruments, systems and procedures for treating a tooth root canal in which the root canal is cleansed of bacteriological materials by physical and acoustic debridgement and flushing with an irrigation solution, particularly the apparatus and equipment for providing irrigation to remove diseased and necrotic tissue.

Endodontic has become an important part of dentistry. Whereas, prior to the common use of endodontic procedures, an abscessed tooth was typically treated only by extraction of the tooth. However since the advancement of endodontics abscessed teeth can be successfully treated to permit retention by a patient for greatly increased health and physiological benefit. Endodontics has been one of the great advancements in modern medicine.

The endodontic preparation of a root canal typically includes opening the root canal through the coronal area of the tooth and thereafter manipulating files and reamers within the root canal to physically remove as much as possible of the pulpal material. This pulpal material is typically infected or necrotic, that is, dead material and any such material that remains in the root canal after the procedure is completed is a source of potential infection. For this reason the proper treatment of a root canal attempts to remove as much of such necrotic pulpal material as is possible. By use of files and reamers, a substantial portion of such pulpal material can be removed however it is virtually impossible in most cases to remove all such material by physical manipulation of tools within the canal. For this reason, in recent times procedures have been developed wherein the root canal is irrigated or flushed with a fluid to remove and/or neutralize organic pulpal material that remains after files and reamers have been employed.

As background information reference may be had to U.S. Pat. No. 4,330,278 that issued May 18, 1982 to Howard Martin, entitled "Endodontic Flow-Through Ultrasonic Instrument Holder Device." This device shows a system that includes a holder for holding an instrument used for dental work that includes a passageway by which flushing fluid can be injected into a tooth during endodontic procedures. The present invention is an improvement on this basic concept as revealed in this U.S. patent.

Current tip assembly designs for delivering a flushing fluid to a root canal—for example, U.S. Pat. No. 6,948,935 that issued Sep. 27, 2005 to John Nusstein, entitled "Ultrasonic Dental Device"—do not effectively transfer the ultrasonic energy to the flushing fluid and prove awkward to use because of the tip assembly configuration and tubing assembly arrangement. The present invention is also an improvement on those tip assembly designs.

BRIEF SUMMARY OF THE INVENTION

The invention herein is a system and a method for simultaneous liquefaction and acoustic debridgement of a tooth root canal. The system includes a manipulatible hand piece having a flow passageway therethrough. An ultrasonic energy generator is secured to the hand piece. A flexible injection tube is dimensioned and configured for insertion into a tooth root canal. A coupler is employed for removably affixing the proximal end of the injection tube to a hand piece. A pressurized source of flushing fluid is connected to the hand piece by which fluid having ultrasonic energy imposed thereon is forced into the root canal.

An important improvement in the invention herein is the provision of a system in which fluid is injected into a tooth root canal using pressure pulses that augments the dislodgement and removal of debris contained in the root canal while simultaneously the fluid pressure pulses are superimposed with ultrasonic energy.

Another important improvement is a contra-angle tip assembly that has an internal fluid flow passageway therethrough. A portion of the passageway is partially encircled by a receiver end of a tip assembly insert. This arrangement serves to directly transfer the ultrasonic energy to the fluid. The design of the tip assembly also allows for a supply tube to run substantially parallel to the hand piece and, therefore, out of the way of a clinician as the clinician manipulates the hand piece.

A more complete understanding of the invention will be obtained from the following detailed description of the preferred embodiments taken in conjunction with the drawings and attached claims.

BRIEF DESCRIPTION OF THE DRAWINGS

FIG. 4 is a chart illustrating the pressure of irrigation fluid injected into a tooth root canal by the systems and methods of this invention and shows pressure pulses having superimposed ultrasonic energy thereon.

FIG. 5 is a cross-sectional view of a tip assembly designed to directly transfer the ultrasonic energy to the irrigation fluid. The fluid flow passageway extends from an inlet end to (and past) an outlet end of the tip assembly. Located between the inlet end and outlet end is a receiver that a portion of the passageway passes through and makes contact with.

FIG. 7 shows an alternate embodiment of the tip assembly wherein the portion of the injection tube which extends past the outlet end is replaced by an injection needle. The inlet port, outlet port, and tubular body may be separate pieces which are joined together.

FIG. 8 is a view of the supply tubes that connect the pressurized fluid source with the inlet end of the tip assembly. Tube guides may be used to properly position and hold the tubing in place.

DETAILED DESCRIPTION OF THE PREFERRED EMBODIMENTS

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements shown by the drawings are identified by the following numbers:

| 10 | tooth |
|---|---|
| 12 | coronal area |
| 14 | roots |
| 16 | open area |
| 18 | root canal |
| 20 | root canal |
| 22 | apex |
| 24 | hand piece |
| 26 | tubular body portion |
| 28 | flow passageway |
| 30 | internal threads |
| 32 | enlarged portion |
| 34 | coupling nut |
| 36 | passageway |
| 38 | flexible injection tube |
| 40 | enlarged end portion |
| 42 | distal end |
| 44 | ultrasonic generator |
| 46 | passageway |
| 48 | power cord |
| 50 | reservoir |
| 52 | pump |
| 54 | conduit |
| 56 | supply tube |
| 58 | power plug |
| 60 | cylinder |
| 62 | piston |
| 64 | motor |
| 66 | shaft |
| 68 | crank arm |
| 70 | piston rod |
| 72 | inlet valve |
| 74 | outlet valve |
| 76 | pressure pulses |
| 78 | passageway |
| 80 | tip assembly |
| 82 | inlet elbow |
| 84 | inlet end |
| 86 | outlet elbow |
| 88 | outlet end |
| 90 | tubular body portion |
| 91 | flat |
| 92 | neck |
| 93 | proximal end |
| 94 | insert |

-continued

| 96 | threaded portion |
|---|---|
| 98 | neck |
| 99 | distal end |
| 100 | receiver |
| 102 | injection tube |
| 104 | beveled surface |
| 106 | supply tube |
| 108 | supply tube |
| 110 | tube guides |
| 112 | needle |
| 114 | sleeve |

Figure 1:
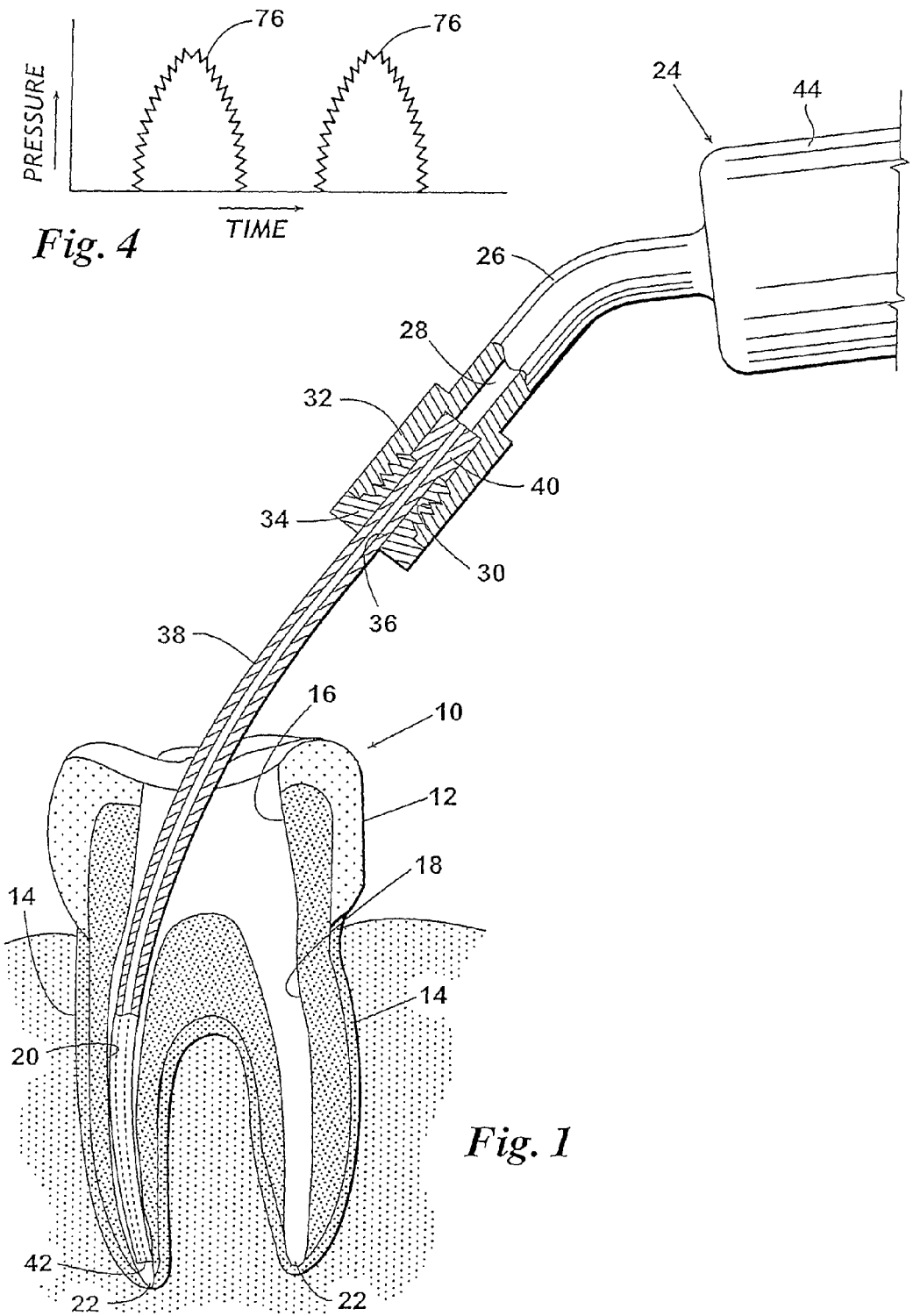
FIG. 1 is a partial cross-sectional view of a hand piece by which an irrigation fluid may be injected into a tooth root canal. The hand piece has an ultrasonic generator as a part thereof whereby the flushing fluid injected into the tooth root canal is energized with ultrasonic energy.

Referring to the drawings and first to FIG. 1, a typical tooth 10 is illustrated in cross-section. The tooth includes a coronal area 12 and roots 14 extending therefrom. The coronal area has an open area 16 that has been drilled to provide access to the upper end of root canals 18 and 20. These root canals 18, 20 extend to the apex 22 of each of the canals.

The practice of endodontic includes, as an important part thereof, preparation of root canals 18 and 20 to receive filler material. Such filler material is typical gutta percha but other comparable materials have been developed. It is important that the root canals 18 and 20 be shaped and cleaned as thoroughly as possible to remove all organic material. Such organic material is typically pulpal material that exists as a natural portion of a tooth and by which a tooth is nourished during the formation process. Such pulpal material, if left within a root canal and entrapped by filler material, can become infected and thereby cause problems to the patient. The infection that originates within a root canal can spread to other parts of the body. For this reason, it is important, as above stated, to remove as much pulpal and other necrotic material from the confines of the root canals 18 and 20 as is possible.

The typical endodontic procedure requires the endodontist to scrape and shape the root canals in a way to remove as much as possible of pulpal material and to shape the root canal to receive filler material. However, though not shown in FIG. 1, root canals 18 and 20 typically have laterally extending fissures and other irregularities in which pulpal material can become entrapped and so that it is very difficult to remove all pulpal material by physically scraping and shaping alone.

For this reason, a procedure has arisen wherein after a root canal is cleansed and shaped mechanically, the root canal is then flushed. For use in flushing a tooth root canal by the methods of this invention, a hand piece, generally indicated by the numeral 24, is employed. Hand piece 24 includes a tubular body portion 26 that has a flow passageway 28 therethrough. The distal end of the tubular body portion is slightly enlarged and provided with internal threads 30, the enlarged portion being indicated by the numeral 32.

Threadably received within the outer end of enlarged portion 32 is a coupling nut 34 that has passageway 36 through it. An injection tube 38 has an integral enlarged end portion 40. The flexible injection tube extends through passageway 36 in the coupling nut which engages enlarged end portion 40 so that the flexible injection tube 38 is connected to the outer end of hand piece tubular body portion 26. The flexible injection tube 38 is elongated and may, as indicated, be tapered towards the distal end 42 that is configured to reach as near as possible to the lower end portions of root canal 18, 20.

Hand piece 24 further includes, as a part of the body portion, an ultrasonic generator 44 that has the capacity to generate ultrasonic sound energy in the form of vibrations. The sound vibrations from ultrasonic generator 44 are coupled to the hand piece tubular body portion and to flexible injection tube 38.

Figures 2, 3:
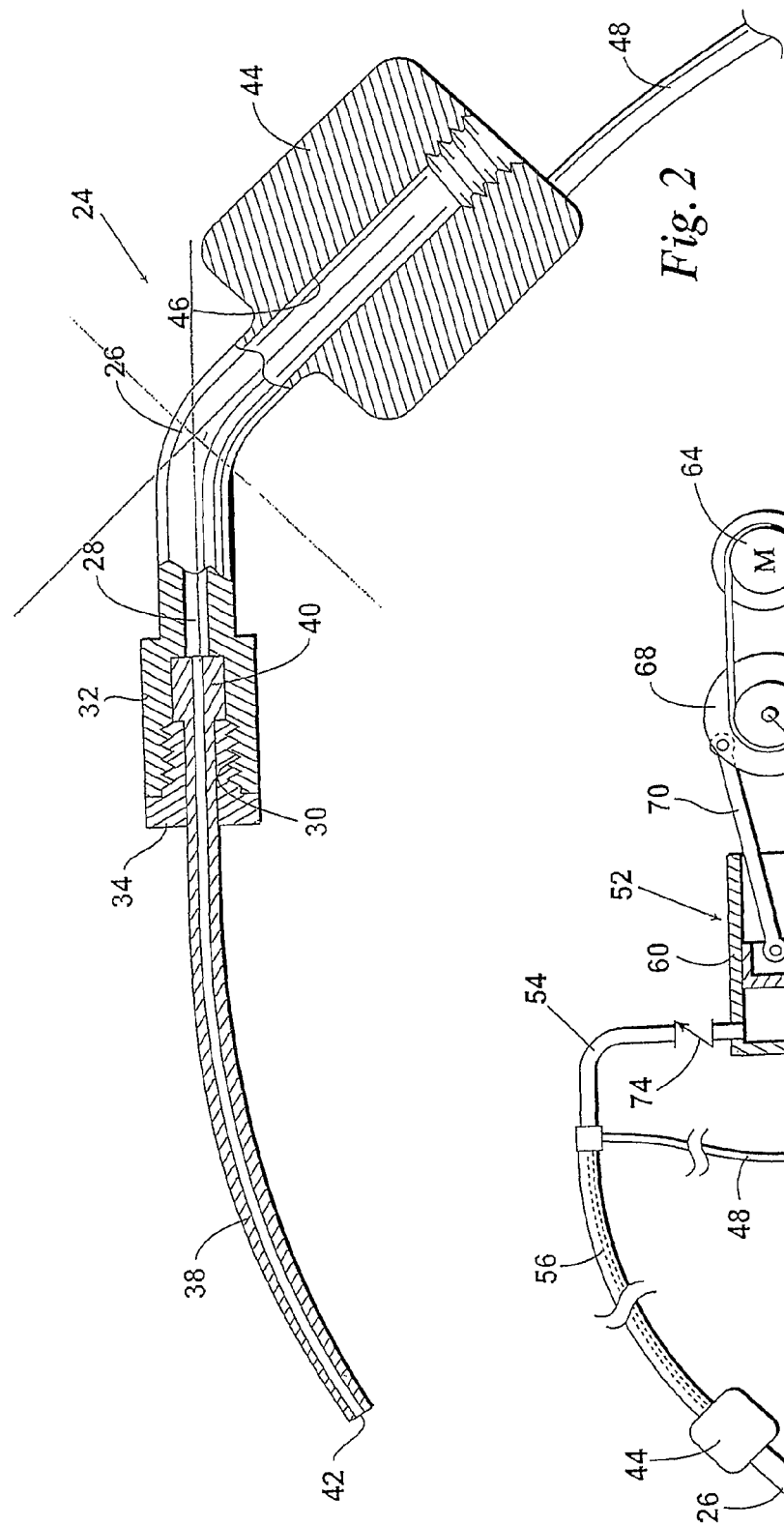
FIG. 2 shows the hand piece as illustrated in FIG. 1 with an ultrasonic generator having provision to accommodate the flow of flushing fluid therethrough.
FIG. 3 is a diagrammatic view of a system for employing the invention. This figure shows a positive displacement pump that forces irrigation fluid under pulsed pressure for injecting into a tooth's root canal. This figure further shows electrical energy applied to the hand piece ultrasonic generator whereby ultrasonic energy is applied to the hand piece and to the flushing liquid.

FIG. 2 shows the hand piece 24 that has been described and shows a passageway 46 extending through ultrasonic generator 44. Thus, passageway 46 is in communication with the tubular body portion flow passageway 28 which in turn communicates with the flexible injection tube 38. A power cord 48 supplies electrical energy to ultrasonic generator 44

FIG. 3 shows diagrammatically the method of practicing the invention. The hand piece 24 is shown diagrammatically with flexible injection tube 38 and ultrasonic generator 44. The system is shown by which liquid may be injected through the hand piece 26 and thereby the flexible injection tube 38 for passage into the root canal of a tooth as shown in FIG. 1 for purposes of flushing the tooth as a part of an endodontic procedure.

Fluid for use in flushing a tooth is contained in a reservoir 50. A typical fluid useable for flushing an endodontically prepared root canal is sodium hypochlorite, usually used as a diluted solution. A pump 52 is employed for moving fluid from reservoir 50 by way of a conduit 54 to a supply tube 56 whereby the fluid is conveyed to hand piece 24, fluid passing through ultrasonic generator 44. Supply tube 56 is shown to carry with it a conductor for electrical energy supplied by a power plug 58. While pump 52 may be a variety of different types a preferred practice of the invention employs a positive displacement pump 52 that includes a cylinder 60 and a piston 62. A motor 64 drives a shaft 66 that has a crank arm 68. Extending from crank arm 68 is a piston rod 70. Pump 52 further includes an inlet valve 72 and an outlet valve 74.

When motor 64 is energized, piston 62 is reciprocated. On each reverse stroke liquid is drawn from tank 50 through intake valve 52 and on the forward or power stroke intake valve 52 is closed and the liquid is forced from the interior of cylinder 64 through outlet valve 74. The liquid passing through conduit 54, supply tube 56, ultrasonic generator 44, tubular body portion 26 and out through the distal end 42 of flexible injection tube 38.

As previously stated, pump 52 may be a variety of pumps but a preferred practice of the invention employs a positive displacement pump to thereby cause the fluid flow through the system to be in a series of pressure pulses as contrasted with substantially constant pressure fluid flow. FIG. 4 is a chart showing the preferred practice of the invention wherein the abscissa is time and the ordinate is pulse pressure showing that the pressure on the fluid passing into a root canal is a sequence of pulses that vary in frequency directly proportional to the rate pump 64 is rotated. Further, an important aspect of the invention is that the fluid injected into a root canal has pressure pulses having superimposed ultrasonic forces. FIG. 4 shows the pressure relationship of the liquid passing into a root canal of the system of this invention in which the abscissa is time and the ordinate is fluid pressure. This figure illustrates the variation in fluid pressure as a consequence of the positive displacement pump showing a sequence of pulses created when piston 62 moves forward separated by periods of low or substantially zero pressure as piston 62 is moved rearwardly. The result is a series of rapid sequential pressure pulses. A unique feature of this invention is the provision of pressure pulses having ultrasonic energy imposed thereon.

The use of ultrasonic energy for improving endodontic procedures is documented in U.S. Pat. No. 4,330,278. The concept herein is to provide a system of flushing or irrigating a root canal in a way to maximize removal and neutralization of organic material. Further, the solution by which the canal is washed is preferably one that removes and neutralizes necrotic tissue so as to reduce the chance that the root canal will have bacteria therein when it receives the filler material after the canal has been properly prepared. The use of sodium hypochlorite to react with necrotic tissue is well known. In addition to sodium hypochlorite other chemical solutions may be employed and sodium hypochlorite is illustrated herein as a typical solution that has the capacity to react with and neutralize necrotic material while having minimal effect on non-necrotic tissue in the body.

The rate of pressure pulses employed in the practice of the invention can vary substantially from a relatively low frequency of two or three pulses per second to a high frequency such as 50 to 100 pulses per second. The ultrasonic frequency rate can also vary but typically is at a frequency above 20,000 Hz.

The ultrasonic generator as indicated in FIGS. 1 and 2 is diagrammatic only since such apparatus is known in the industry and readily commercially available. The flow of fluids through the channels provided in the system forms an effective pathway for the transmission of ultrasonic energy since ultrasonic signals flow through a liquid medium with little resistance as is readily indicated by the success of sonar and other apparatus for measuring using sound energy transmitted through water.

Figure 6:
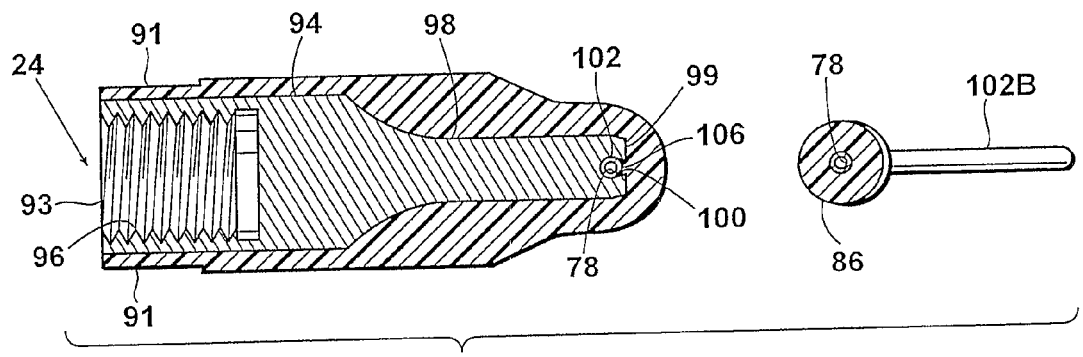
FIG. 6 is a view taken along section line 6-6 of FIG. 5. A C-shaped receiver located at the distal end of the insert tightly receives a portion of the fluid flow passageway.
Figure 5:
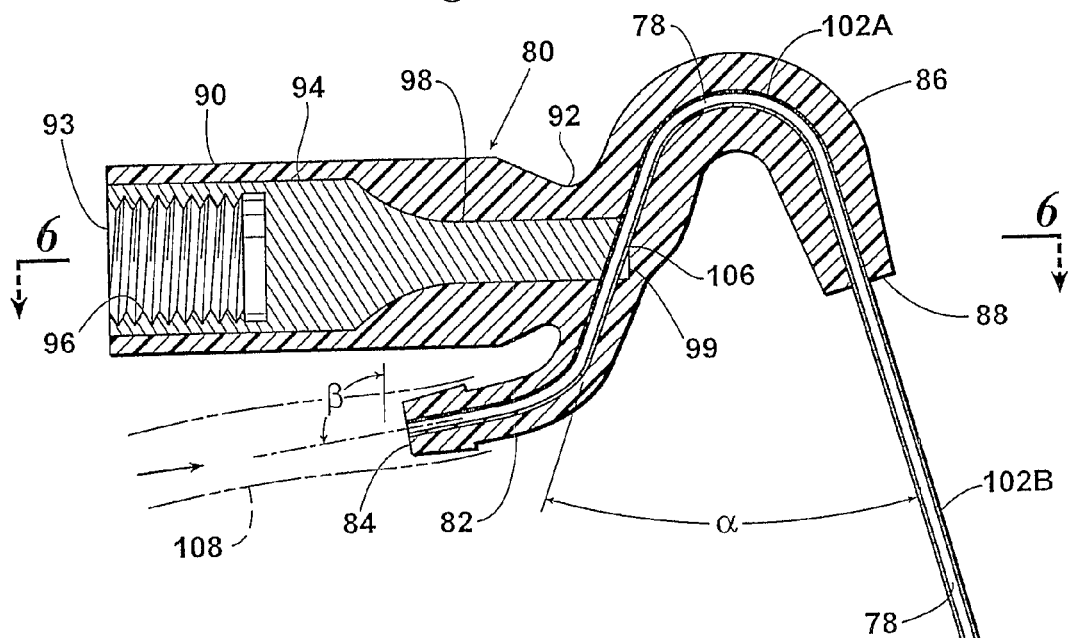

Referring now to FIGS. 5 and 6, a contra-angle tip assembly 80 for use with the system described herein is illustrated. Tip assembly 80 includes a tubular body portion 90 having an inlet end 84, an outlet end 88, and a reduced neck portion 92. Inlet end 84 is preferably generally located in a different horizontal plane than outlet end 88. The contra-angle α is preferably an acute angle, with outlet elbow 86 having a goose-neck shape. Inlet elbow 82 has an angular bend β. Inlet elbow 82 and outlet elbow 86 each contain a portion of an injection tube 102 that passes through the interior of tip assembly 80. Injection tube 102 has a fluid flow passageway 78 passing therethrough. A portion 102A of injection tube 102 lies between inlet end 84 and outlet end 88, and another portion 102B extends past outlet end 88. Portion 102B preferably has a beveled surface 104 at its distal end 42.

As injection tube 102 extends in a curvilinear manner from inlet end 84 to outlet end 88, a portion 106 of injection tube 102 passes through a receiver 100 of insert 94. Insert 94, which is preferably solid and made of brass, is a tubular shaped insert with a reduced neck portion 98. A threaded portion 96 at the proximal end 93 of insert 94 helps secure tip assembly 80 to hand piece 24. Tubular body portion 90 preferably includes flats 91 for receiving a wrench (not shown) and securing tip assembly 80 to hand piece 24. Receiver 100 is preferably a C-shaped receiver and is located at the distal end 99 of insert 94. A portion 106 of injection tube 102 is partially encircled by C-shaped receiver 100, thereby placing insert 94 in contact with portion 106 of injection tube 102. Ultrasonic energy generated by ultrasonic generator 44 (see FIG. 1) may therefore pass from insert 94 to injection tube 102. Receiver 100 may have a U-shape or some other shape designed to receive and be in contact with portion 106.

Receiver 100 may be crimped about portion 106 to securely hold injection tube 102 yet still maintain the integrity of fluid flow passageway 78. Tubular body portion 90 of tip assembly 80 is preferably formed of a polymer and surrounds insert 94 and portion 102A of injection tube 102. If formed of a polymer, tubular body portion 90 helps to dampen vibration passing through insert 94 and injection tube 102.

FIGS. 7 and 8 illustrate an alternate preferred embodiment of tip assembly 80. Rather than being integrally formed as part of tubular body portion 90, inlet elbow 82 and outlet elbow 86 are separate components which are joined to tubular body portion 90. Inlet elbow 82, outlet elbow 86, and tubular body portion 90 may be a polymer material or a metal. As injection tube 102 extends in a curvilinear manner from inlet end 84 to outlet end 88, a portion 106 passes through and is partially encircled by insert 94 (not shown; see FIGS. 5 and 6). A sleeve 114 connects a needle 112 to outlet end 88. Fluid flow passageway 78 passes through injection tube 102 and needle 112. Alternatively, needle 112 may be replaced by a second section of injection tube 102 having a beveled surface 104 at its distal end (see e.g., FIG. 5). For example, portions 102A and 102B may be a single piece of injection tube or may be two separate pieces of injection tube. In yet another preferred embodiment of tip assembly 80, fluid flow passageway 78 is not formed by injection tube 102 but rather is formed integral to inlet elbow 82, tubular body portion 90, and outlet elbow 86.

To connect tip assembly 80 to fluid reservoir 50 (see FIG. 1), supply tubes 106 and 108 may be provided. Supply tube 108 is preferably a smaller diameter tube than supply tube 106. Tube guides 110 secure the supply tubes 106 and 108 in their proper position relative to hand piece 24 and inlet elbow 82. Tube guides 110 are preferably silicon tube guides. As pump 52 pumps fluid from reservoir 50, the pressurized fluid flows through supply tubes 106 and 108 and into flow passageway 78. The arrangement of the inlet end 84 and outlet end 88 of tip assembly 80, as shown in FIGS. 5 to 8, allows supply tube 108 to run substantially parallel to hand piece 24 and, therefore, out of the way of a clinician as the clinician manipulates hand piece 24 during a procedure.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claims, including the full range of equivalency to which each element thereof is entitled.

What is claimed is:

1. A method for simultaneous liquefaction and acoustic debridement of a tooth root canal, the method comprising the steps of:
   (i) after shaping the tooth root canal with an endodontic file, inserting a discharge injection tube into the shaped tooth root canal, the discharge injection tube being connected to an ultrasonic hand piece and having a distal end portion configured for insertion into the shaped tooth root canal;
   (ii) after step (i), passing a flushing fluid under pulsed pressure through the ultrasonic hand piece and into the discharge injection tube while simultaneously superimposing an ultrasonic frequency to the flushing fluid under pulsed pressure; and
   (iii) after step (ii), directing the flushing fluid under pulsed pressure and superimposed ultrasonic frequency so that portions of the shaped tooth root canal not accessible to debridement by the endodontic file are simultaneously liquefied and acoustically debrided of unwanted material.

2. A method according to claim 1 wherein the pulsed pressure is applied at a pressure pulse rate of 2 to 3 pressure pulses per second.

3. A method according to claim 1 wherein the pulsed pressure is applied at pressure pulse rate of 4 to 49 pressure pulses per second.

4. A method according to claim 1 wherein the pulsed pressure is applied at pressure pulse rate of 50 to 100 pressure pulses per second.

5. A method according to claim 1 wherein a flow rate of the flushing fluid through an opening of the discharge injection tube is a flow rate effective for use with the shaped tooth root canal.

6. A method according to claim 1 wherein the portions of the shaped tooth root canal not accessible to debridement by the endodontic file is a laterally extending fissure of the root canal.

7. A method for simultaneous liquefaction and acoustic debridement of a tooth root canal, the method comprising the steps of:
   (i) inserting a discharge injection tube into a tooth root canal, the discharge injection tube being connected to an ultrasonic hand piece and having a distal end portion configured for insertion into the root canal;
   (ii) after step (i), passing a flushing fluid under pulsed pressure through the ultrasonic hand piece and into the discharge injection tube while simultaneously superimposing an ultrasonic frequency to the flushing fluid under pulsed pressure; and
   (iii) after step (ii), directing the flushing fluid under pulsed pressure and superimposed ultrasonic frequency so that laterally extending fissures of the root canal are simultaneously liquefied and acoustically debrided of unwanted material.

\* \* \* \* \*